United States Patent [19]

Wilson

[11] Patent Number: 5,501,597
[45] Date of Patent: Mar. 26, 1996

[54] DENTAL INSTRUMENT WITH GRIPPING HANDLE AND METHOD FOR MANUFACTURING SAME

[75] Inventor: Roselyn Wilson, Lakeville, Minn.

[73] Assignee: Minnesota Prophy Power, Inc., Lakeville, Minn.

[21] Appl. No.: 236,494

[22] Filed: Apr. 29, 1994

[51] Int. Cl.⁶ .................................................. A61C 3/00
[52] U.S. Cl. .................................................. 433/141
[58] Field of Search .................................. 433/102, 141, 433/224, 143, 144, 147, 164; 16/110 R, DIG. 12, DIG. 18, DIG. 19; 81/489, 177.1

[56] References Cited

U.S. PATENT DOCUMENTS

| | | | |
|---|---|---|---|
| 171,106 | 12/1875 | Donaldson | 40/913 |
| 2,609,851 | 9/1952 | Hadfield | 81/489 |
| 3,721,006 | 3/1973 | Malmin | 433/141 |
| 4,283,808 | 8/1981 | Beebe | 15/145 |
| 4,759,713 | 7/1988 | Heiss et al. | 433/141 |
| 4,882,867 | 11/1989 | Lindén | 40/913 |
| 5,090,907 | 2/1992 | Hewitt et al. | 433/144 |

FOREIGN PATENT DOCUMENTS

| | | | |
|---|---|---|---|
| 2635998 | 3/1990 | France | 81/177.1 |
| 4119311 | 12/1991 | Germany | 433/143 |

OTHER PUBLICATIONS

Thompson Dental Manufacturing Co, Inc. Catalog, 5–1984.
One page Sales Brochure from Thompson Instruments.
Photocopy of a Thompson Instruments Dental Curette.

*Primary Examiner*—Cary E. O'Connor
*Attorney, Agent, or Firm*—Palmatier, Sjoquist & Helget

[57] ABSTRACT

A dental instrument having a pair of elastomeric gripping handles is disclosed. The instrument is comprised of an elongate shaft with two end portions and two ends, the two end portions have knurled surfaces. Work pieces having shanks and working tips extend out the open ends of the shaft, the intersection of the workpiece and shaft defining a junction. Elastomeric gripping handles surround the shaft at the end portions, enclose the junctions, have cylindrical portions on the end portions and conical transition portions that taper onto the shanks of the workpieces.

12 Claims, 3 Drawing Sheets

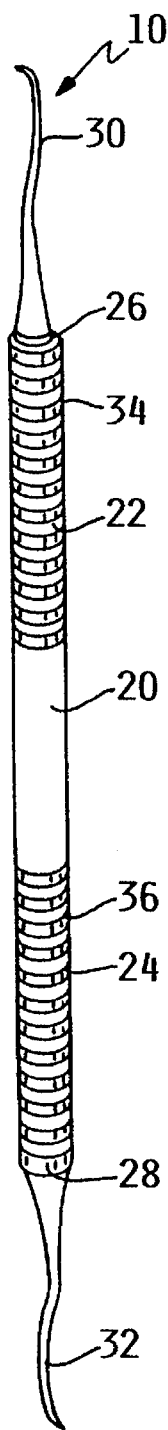
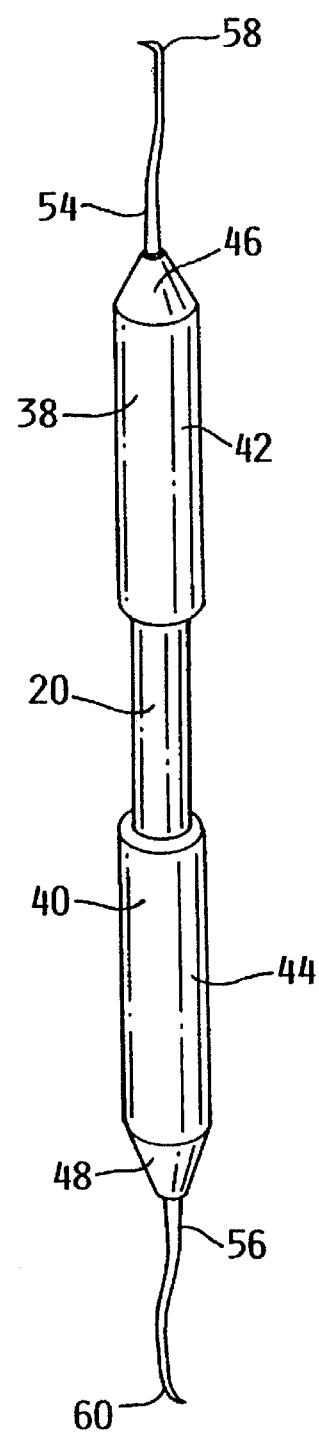
FIG. 1
(PRIOR ART)
FIG. 2

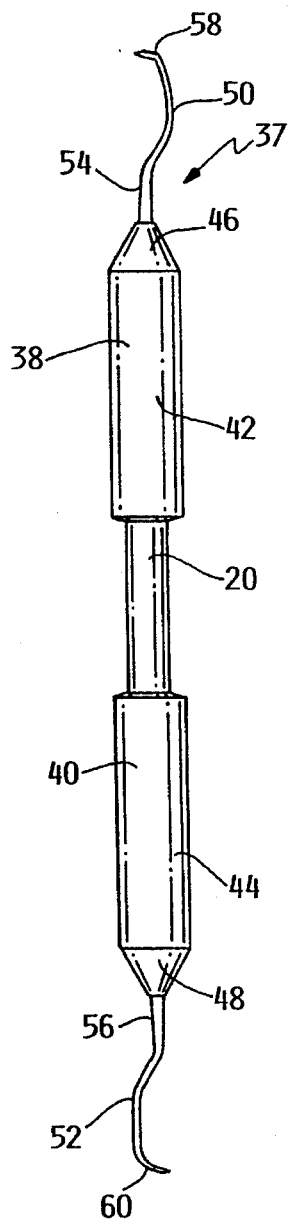
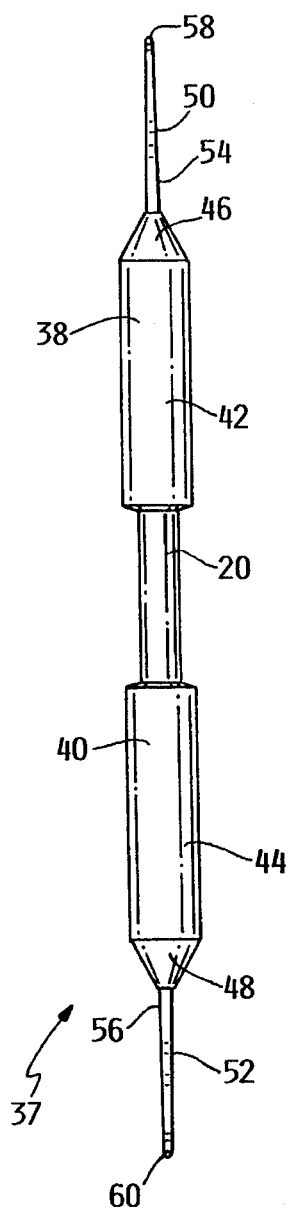
FIG. 3     FIG. 4
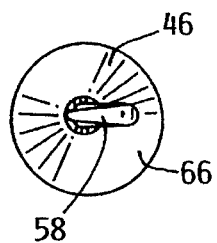
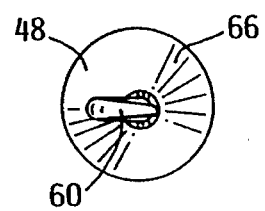
FIG. 5     FIG. 6

5,501,597

DENTAL INSTRUMENT WITH GRIPPING HANDLE AND METHOD FOR MANUFACTURING SAME

BACKGROUND OF THE INVENTION

This invention relates to dentistry, more particularly the invention relates to dental instruments with gripping handles and a method for manufacturing same.

Hand-held instruments typically used by dentists and dental hygienists include curettes, universals, scaler and explorers. All of these dental instruments have an elongate shaft with various styles of workpieces extending out oft the ends of said shafts. The shank and end of the shaft are not knurled or otherwise textured having smooth stainless steel surfaces. The instruments are generally used in a modified pencil grip with the middle finger providing pressure on the shank of the workpiece or proximate to the end of the shaft. Users will often move their middle finger between the end of the shaft and the shank depending on various factors including the region of the mouth they are working on and the pressure needed. Gripping of these instruments directly on the stainless steel shaft has been facilitated by knurled or otherwise textured surfaces. The relatively slender configuration of the shafts and the required delicate but firm utilization of these instruments in dental work has led to cumulative trauma injuries such as carpel tunnel. The metal surface can also be slippery, especially when moistened, such as by saliva, requiring an even tighter grip on the conventional style dental instruments. The slipperiness problem is exacerbated by latex gloves which have very high slipperiness when used on stainless steel in the presence of moisture.

U.S. Patent No. 5,090,907 issued to Fred G. Hewitt et al. discloses a finger pad proximate to the workpiece that was resilient and could rotate about the shaft of the dental instrument. Said pad is only configured to receive a single finger and does not easily accommodate the sliding of the middle finger from the pad to the shank of the workpiece. Padding was not provided for the other fingers utilized in the gripping of the dental instrument.

SUMMARY OF THE INVENTION

A dental instrument having a pair of elastomeric gripping handles is disclosed. The instrument is comprised of an elongate shaft with two end portions and two ends, the two end portions have knurled surfaces. Work pieces having shanks and working tips extend out the open ends of the shaft, the intersection of the workpiece and shaft defining a junction. Elastomeric gripping handles surround the shaft at the end portions, enclose the junctions, have cylindrical portions on the end portions and conical transition portions that taper onto the shanks of the workpieces.

An object and advantage of the invention is that the conical portion provides a significantly improved base for the middle finger, both in contact area and comfort.

A further object and advantage of the invention is that the overall gripability of the dental instrument is substantially improved over conventional dental instruments.

An additional object and advantage of the invention is that existing dental instruments may be easily and inexpensively adapted to incorporate the invention. Said adaption may be accomplished without modification of the dental instrument other than adding the gripping handles.

An additional object and advantage of the invention is that the junction between the workpiece and the shaft is encapsulated by the thermoplastic material minimizing the potential for foreign material lodging or accumulating in this region.

An additional object and advantage of the invention is that there is a very smooth transition between the handle of the instrument and the workpiece providing optimal comfort, especially at the middle finger.

BRIEF DESCRIPTION OF THE DRAWINGS

FIG. 1 is perspective of a conventional prior art curette.

FIG. 2 is perspective view of a dental curette incorporating the invention.

FIG. 3 is a front view of the dental curette incorporating the invention.

FIG. 4 is side view of the dental curette incorporating the invention.

FIG. 5 is top view of the dental curette incorporating the invention.

FIG. 6 is bottom view of the dental curette incorporating the invention.

DETAILED DESCRIPTION OF THE PREFERRED EMBODIMENTS

Figure 7:
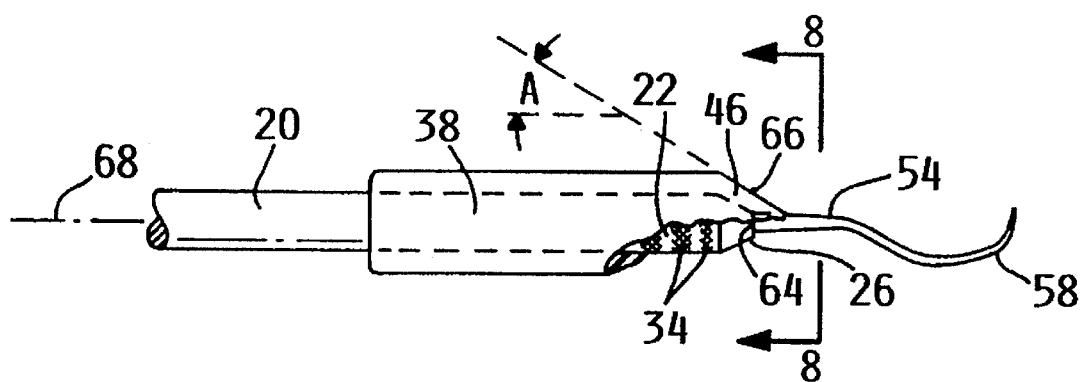
FIG. 7 is a plan view of a portion of a dental curette incorporating the invention with a portion of the gripping handle broken away.
Figure 8:
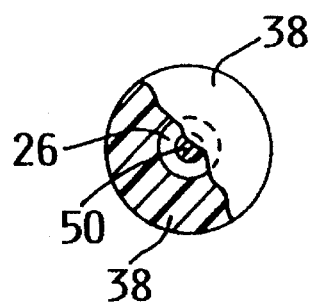
FIG. 8 is a sectional view taken through plane 8—8 of FIG. 7 with a portion of the gripping handle broken away.

Referring to FIG. 1, a typical dental instrument is shown designated generally by the numeral 10, and is comprised of an elongate shaft 20 having opposing end portions 22, 24, ends or collars 26, 28 and two workpieces 30, 32 extending from the collars 26, 28. The end portions 22, 24 have knurled surfaces 34, 36 to aid in gripping the shaft 20. The instrument 10 depicted is a dental curette.

Referring to FIGS. 2, 3, 4, 5, and 6, the invention is shown, is generally indicated by the numeral 37 and has in addition to the elements of the instrument described above, two gripping pads or handles 38, 40 located generally on the end portions 22, 24 of the shaft 20. The end portions are covered and not shown in FIGS. 3–6. The gripping pads have a cylindrical portion 42, 44 and integral conical portions 46, 48 extending out of the conical portions 46, 48 are the workpieces 50, 52. The workpieces have shanks 54, 56 and work-tips 58, 60.

FIGS. 5 and 6 show a top view and a bottom view of the dental instrument incorporating the invention.

FIG. 7 shows a partial sectional of the dental instrument incorporating the invention with the portion of the gripping pad broken away to reveal the knurled surfaces 34 on the end portion 22 of the shaft 20, The gripping pad or handle 38 extends over and encapsulates the junction 64 between the workpiece 50 and the end or collar 26.

FIG, 8 shows a partial sectional taken at plane 8—8 of FIG. 7 with a portion of the gripping pad 38 cut away. An angle A is formed by the outside surface 66 of the conical portion on the shaft axis 68, A suitable angle is 30 degrees to 45 degrees, This angle between the conical portion and shaft axis provides sufficient contact surface for the middle finger and also permits the conical surface and the cylindrical portion to be in close proximity to the workpiece, A lesser angle provides more taper and positions the cylindrical portion more distally than the ideal from the workpiece and lessens the effective width of the conical portion contacted by the middle finger, A greater angle reduces the length of the conical portion and lessens the efficiency of the transfer of pressure by the middle finger from the conical portion to the work-tip, The range of 30° to 45° appears to be the optimal taper, An appropriate diameter for the cylindrical portion is 0.40 to 0.45 inches.

A suitable thermoplastic material for the preferred embodiment is a styrene-ethylene/butylene-styrene block copolymer such as the Kraton® G rubber compound available from Shell Chemical Company. This material provides sufficient gripability, adhesion to the shaft 20, and rigidity.

Existing dental instruments may suitably be modified to incorporate the invention by adding the elastomeric gripping handles 38.

The gripping pads or handles are assembled onto the dental instruments by placing the dental instrument in a suitable mold that seals off the instrument at the shank and the shaft and a suitable thermoplastic material is injected into a mold suitably shaped mold cavity by conventional means.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A dental instrument comprising:
   (a) an elongate shaft having an end portion and a collar;
   (b) a dental workpiece extending from the collar of the shaft, the workpiece comprising a shank and work-tip; and
   (c) a gripping handle extending from the end portion of the shaft to the shank of the workpiece, the gripping handle surrounding and adhering to the end portion of the shaft, to the collar, and to the workpiece at the shank.

2. The dental instrument of claim 1, wherein the end portion of the shaft has a knurled surface to which the gripping handle is adhered.

3. The dental instrument of claim 1, wherein the gripping handle is formed of an elastomeric material, has a substantially cylindrical portion surrounding the end portion and a tapered portion extending around the shank.

4. The dental instrument of claim 1, wherein the elongate shaft and the workpiece comprise a dental curette and wherein the gripping handle is injection molded over the end portion and shank of said dental curette.

5. The dental instrument of claim 1 wherein the substantially cylindrical portion has a diameter of at least 0.40 inches.

6. The dental instrument of claim 1, wherein the elastomeric material is an injection moldable thermoplastic elastomer.

7. A dental instrument comprising:
   (a) an elongate shaft having a collar and an end portion adjacent to the collar;
   (b) a dental workpiece extending from the collar, the workpiece comprising a shank and work-tip, the shank and collar converging at a junction; and
   (c) a gripping pad formed of an elastomeric material, the gripping pad surrounding and adhering to the end portion of the shaft encapsulating the junction and further having a portion that tapers onto the shank of the workpiece.

8. The dental instrument of claim 7, wherein the gripping pad includes a cylindrical portion surrounding the end portion.

9. The dental instrument of claim 8, wherein the shaft has an axis and the conical portion has an exterior surface and the exterior surface of the conical portion has an external surface, and wherein the external surface of the conical portion forms an angle with the axis of the shaft, said angle being within the range of 30 degrees to 45 degrees.

10. The dental instrument of claim 7 wherein the end portion of the shaft has a knurled surface.

11. A process for adding a gripping pad to an existing dental instrument, the existing dental instrument having an elongate shaft with an end portion, a collar, and a workpiece extending from the collar at a junction, the process comprising:
   (a) placement of the dental instrument in an elongate, mold cavity having a substantially cylindrical portion and a conical portion, the dental instrument placed coaxial with the mold cavity such that the shank is extending out of the conical portion and the end portion is within the cylindrical portion;
   (b) injection into the mold cavity of a thermoplastic material whereby a gripping pad is formed on said dental instrument extending from the end portion to the workpiece and encapsulating the junction.

12. The process of claim 11, wherein the thermoplastic material is a styrene-ethylene/butylene-styrene block copolymer.

* * * * *

UNITED STATES PATENT AND TRADEMARK OFFICE
CERTIFICATE OF CORRECTION

PATENT NO.   : 5,501,597
DATED        : March 26, 1996
INVENTOR(S)  : Roselyn Wilson It is certified that error appears in the above-indentified patent and that said Letters Patent is hereby corrected as shown below:

Column 1, line 13, delete "oft" and replace it with --of--.

Column 2, line 48, please insert "." after --48--; and delete the "e" in extending and insert therefor --E--.

Column 2, line 56, after --20--, please delete "," and replace it with ".".

Column 2, line 62, after --68--, please delete "," and replace it with ".".

Column 2, line 63, after --degrees, please delete "," and replace it with ".".

Column 2, line 66, after --workpiece-- please delete "," and replace it with ".".

Column 3, line 4, after --finger-- please delete "," and replace it with ".".

Column 3, line 7, after --work-tip-- please delete "," and replace it with ".".

Column 3, line 8, after --taper-- please delete "," and replace it with ".".

Signed and Sealed this

Eleventh Day of June, 1996

Attest:

BRUCE LEHMAN

*Attesting Officer*          *Commissioner of Patents and Trademarks*